United States Patent [19]
Jemmott

[11] Patent Number: 5,826,621
[45] Date of Patent: Oct. 27, 1998

[54] VALVE APPARATUS

[75] Inventor: Gilbert F. Jemmott, San Marcos, Calif.

[73] Assignee: Alaris Medical Systems, Inc., San Diego, Calif.

[21] Appl. No.: 692,503

[22] Filed: Aug. 5, 1996

[51] Int. Cl.$^6$ ................................................. F16K 15/14
[52] U.S. Cl. ......................... 137/853; 251/342; 604/247
[58] Field of Search .................... 137/853, 852, 137/522, 523; 251/342; 604/247, 256, 246, 30, 31

[56] References Cited

U.S. PATENT DOCUMENTS

| | | | |
|---|---|---|---|
| 2,518,165 | 4/1950 | Millard | 251/342 |
| 2,999,499 | 9/1961 | Willet . | |
| 4,065,093 | 12/1977 | Phillips | 251/342 |
| 4,106,675 | 8/1978 | Taylor . | |
| 4,142,645 | 3/1979 | Walton . | |
| 4,381,591 | 5/1983 | Barger et al. . | |
| 4,527,588 | 7/1985 | Tseo et al. . | |
| 4,730,635 | 3/1988 | Linden . | |
| 4,913,401 | 4/1990 | Handke | 251/342 |
| 5,020,562 | 6/1991 | Richmond et al. | 604/247 |
| 5,022,422 | 6/1991 | Di Palma | 251/342 |
| 5,265,847 | 11/1993 | Vorhis . | |
| 5,396,925 | 3/1995 | Poli | 251/342 |

FOREIGN PATENT DOCUMENTS

| | | |
|---|---|---|
| 2456525 | 12/1980 | France . |
| 160807 | 11/1985 | Sweden . |
| WO 9516480 | 6/1995 | WIPO . |

OTHER PUBLICATIONS

PCT International Search Report for PCT/US97/13252.

*Primary Examiner*—Denise L. Ferensic
*Assistant Examiner*—Joanne Y. Kim
*Attorney, Agent, or Firm*—Fulwider Patton Lee & Utecht, LLP

[57] ABSTRACT

A valve apparatus employs a spherical sealing element disposed in resiliently deformable tubing. The dimensions of the sealing element are selected such that the valve opens when subjected to a cracking pressure that is greater than the head pressure developed in an IV set and less than the pressure generated by a peristaltic pump. The valve additionally has an actuator element associated therewith that may be applied to the tubing about the sealing element to cause free flow without the need for continuous manipulation.

40 Claims, 4 Drawing Sheets

VALVE APPARATUS

BACKGROUND OF THE INVENTION

The present invention relates generally to valves used in controlling the flow of a fluid through a conduit and, more particularly, to valves of the type wherein a tight-fitting sealing element is held in position within resiliently deformable tubing to form a seal therewith.

A variety of valve configurations have been devised that utilize a ball to seal the interior of resiliently deformable tubing. The diameter of the ball is selected to be slightly larger than the inner diameter of the tubing such that the resulting interference fit is capable of maintaining a seal despite fluid pressure within the tubing. Pinching the tubing about the ball causes the tubing to become compressed against the ball at two diametrically opposed points. Such deformation causes the tubing to flex outwardly in the sections adjacent the compressed areas and thereby create two fluid paths on either side of the ball. Release of the tubing allows the resilient tubing to relax, resume its previous shape about the ball, and reseal the fluid paths thereby stopping fluid flow.

In most cases, a need exists to maintain the ball in a fixed position within the tubing. Failure to do so can result in the ball shifting within the tubing either due to the pressure of fluid against the ball or the pressure placed on the outside of the tubing around the ball to cause flow. Pressure exerted against the exterior of the tubing can cause the ball to move away from the pressure point thereby precluding creation of a fluid path, unless the ball is anchored in place. This can be a particular problem with the use of relatively low friction tubing or ball materials.

A number of different approaches have been utilized in an effort to maintain the ball in a particular position within the tubing. An example thereof comprises a localized increase in the inner diameter of the tubing to house the ball wherein the adjacent sections of reduced diameter tubing prevent the ball from migrating out of position. Inserts, positioned on either side of the ball within the tubing, may similarly be employed to prevent any shifting. However, such tubing width variations or use of inserts can raise manufacturing expense and may cause an increase in assembly expense due to the need to locate the ball precisely at a certain position within the tubing.

A need exists in the medical field for a valve in a fluid administration set that can stop flow through the set when necessary. In many cases, a manual flow stop valve device is provided that can stop flow, allow flow, or allow less than full flow depending on the relative positions of the components of the flow stop valve device. It is also desirable that such a flow stop device be available for operator manipulation so that the administration set can quickly be purged of air before application to the patient by allowing the free flow of the medical fluid through the set and then stopping such flow so that administration to the patient can be performed in a controlled manner.

Such a device may be necessary even when the set is used with a peristaltic pump that always maintains at least one section of the tubing occluded during the pumping process. Both before and after engagement with the peristaltic pump, a flow stop device can be used effectively. Before engagement with the patient, the flow stop device may be engaged with the tubing to prevent the free flow of fluid and then temporarily released to purge the set of air as already mentioned. After the pumping procedure is complete, the flow stop device may again be engaged to prevent the free flow of fluid to the patient after removal of the set from the pump.

An automatically closing configuration has been previously disclosed wherein the ball sealing element formed on a stem mount is rigidly affixed to a fitting of the administration set which in turn is immobilized. The fitting is received in a mounting bracket in a peristaltic pump at a position laterally displaced from and upstream from the peristaltic mechanism. When engaging the tubing with the peristaltic mechanism, the tubing is stretched to one side of the ball thereby pulling one side of the tubing's inner wall away from the ball element to create a fluid path. In normal operation, the tubing is held stretched to one side of the sealing element by the peristaltic pumping mechanism. Such lateral displacement serves to maintain the valve in its open or flow position while disengagement of the tubing from the pump mechanism allows the tubing to relax and once again seal with the ball thereby automatically shutting off the valve and fluid flow.

The above arrangement suffers from a few disadvantages. For example, when the ball seal device is located upstream and flow is allowed through it by a lateral pull, misloading the tubing in the peristaltic mechanism may result in a lateral pull that opens the valve but the peristaltic mechanism may not completely occlude the tubing below the valve thus resulting in uncontrolled flow to the patient. Additionally, if tolerances are not correctly controlled and the ball is made too large or the inner diameter of the tubing too small, the valve will not open and the pump will be unable to deliver fluid.

The valve configurations described above have been employed in a variety of applications, including medical devices such as blood sampling instruments, drainage bags, IV sets and peristaltic pumps. However, each requires the continuous manipulation of the valve by an operator or its continuous interaction with a relatively complex external device such as a peristaltic pump in order to maintain fluid flow through the valve. In some applications, it would be desirable to be able to set the valve into its open state without the necessity for such complex operator interaction. It may be especially advantageous to have such a flow control valve that is normally closed but which automatically opens during the operation of a peristaltic pump and which automatically closes when the pump stops operating or when the tubing is misloaded in the pump. Should the administration set inadvertently not be properly engaged or become disengaged from the peristaltic pump mechanism, the valve would automatically close thereby avoiding a free flow condition. Likewise should the pump operator remove the administration set from the peristaltic pump before closing an upstream flow stop device, the ball valve would automatically close thus avoiding free flow. Finally, should the administration set become misaligned with the pump or should one of the peristaltic fingers fail to completely occlude the flow path during its operational cycle, the flow control valve should prevent the free flow of fluid.

Previous ball-type valves provide no means to open the valve other than by manually pinching the tubing around the ball which has the disadvantage that continuous manipulation by the operator is required to hold the valve open. Moreover, pinching the tubing to open the valve may not be an easy task nor is the step of manually pulling the tubing laterally while holding the ball stationary. A ball-type valve effective in allowing an operator to open the valve with less strength and without continuous manipulation is therefore desirable. A busy nursing staff would prefer a valve configuration the actuation of which is easy to use. Furthermore, because the valve should not pose a significant restriction when installed in line in the administration set, it is desirable to maximize flow therethrough.

Hence, those skilled in the art have recognized the need for a valve that is simple and inexpensive in construction, is easy to use, and is useable in both a continuously open mode as well as an automatically closing mode. The present invention fulfills these needs and others.

SUMMARY OF THE INVENTION

The present invention provides a ball-type valve that is normally in a flow stop configuration but that automatically opens when subjected to a preselected amount of internal fluid pressure. Alternatively, the valve is actuatable so as to maintain a continuous, fully open condition without the need to manually pinch the valve or to subject the valve to the preselected pressure.

The valve of the present invention includes a substantially rigid housing to which resiliently deformable tubing is attached. A sealing element is attached to the housing and extends into the tubing where its sealing surface engages the inner wall of the tubing to form a seal. The outer diameter of the sealing surface, the inner diameter of the tubing, and the resiliency of the tubing are selected such that the application of a preselected amount of internal fluid pressure or "cracking pressure" is required to expand the tubing sufficiently to allow the flow of the fluid around the sealing element and hence through the valve. Such cracking pressure is preselected to be greater than the maximum head pressure generated in the tubing by an elevated fluid reservoir connected to the tubing, but less than the pressure generated by a fluid pumping mechanism engaging the tubing above the valve.

Alternatively, the valve may be held in its fully open position with the engagement of an actuator element to the tubing about the sealing element. Such actuator element includes two opposed surfaces that are separated by a distance that is slightly greater than the outer diameter of the sealing surface yet less than the outer diameter of the tubing. Positioning the actuator element about the tubing adjacent the housing causes pressure to be exerted on the tubing at two points on opposite sides of the sealing element to deform the tubing and open the valve.

The exterior surfaces of the housing may be configured for receipt in a mounting bracket within for example, a peristaltic pump, downstream from the pumping segment. The mounting bracket holds the housing in a fixed position in relation to the pumping mechanism. The actuator element may be attached directly to or tethered to the IV tubing farther downstream such that the actuator can readily be maneuvered so as to engage the tubing about the sealing surface. Alternatively, the actuator element may be attached at other positions so that it may be readily found and used when needed. The sealing member is held in position by a stem rigidly affixed to the sealing member and anchored in the bore of the housing. The surface of the stem and/or its anchor section may be grooved to permit the flow of fluid thereby.

In another aspect, the housing is located in relation to the pumping mechanism so that when the tubing is mounted in the pumping mechanism, it is pulled laterally in relation to the sealing element thereby lowering the cracking pressure while maintaining the cracking pressure above the maximum head pressure generated in the tubing by an elevated fluid reservoir connected to the tubing. In a more detailed aspect, the stem of the valve is selected such that it is rigid and does not bend significantly as the tubing is pulled laterally in the pumping mechanism. This rigidity of the stem retains the sealing element at an angle to the tubing which is now bent laterally by the pumping mechanism and results in a lowered cracking pressure.

In yet another aspect, the stem attached to the sealing element is formed such that it is more flexible in one axis than the other. This increased flexibility in one axis results in the seal between the sealing element and the flexible tubing being maintained as the valve is subjected to bending pressure in that axis during its mounting in a peristaltic pump. The stem will bend somewhat to tend to align with the longitudinal axis of the tubing as it is bent during the mounting process thereby maintaining the seal.

These and other features and advantages of the present invention will become apparent from the following detailed description of a preferred embodiment which, taken in conjunction with the accompanying drawings, illustrates by way of example the principles of the invention.

DETAILED DESCRIPTION OF THE PREFERRED EMBODIMENT

The figures generally show the preferred embodiment of the present invention and illustrate its versatility especially when used in line in an IV set. The valve is extremely simple and inexpensive in construction. Moreover, it is simple to use and is actuatable in at least two different modes of operation.

Figure 1:
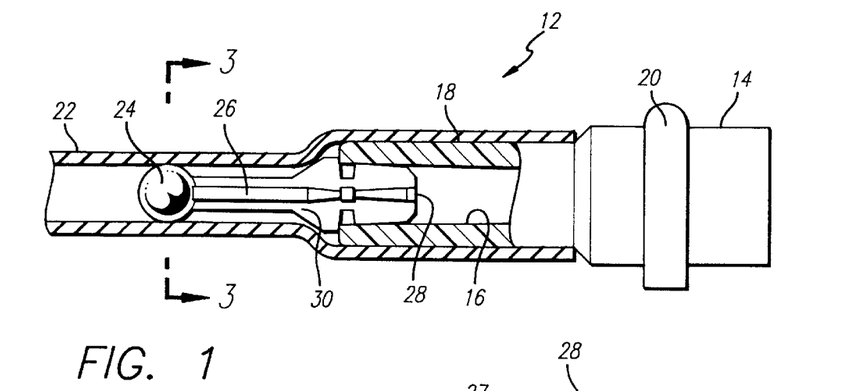
FIG. 1 is a cross-sectional view of a valve apparatus incorporating principles of the present invention, in which the valve is in its closed state.

FIG. 1 is a cross-sectional view showing the valve 12 in its closed state. A rigid, generally cylindrical housing 14 has a bore 16 formed therein to permit the flow of fluid therethrough. The exterior surface of the housing includes a raised collar 20 that provides a surface for immobilizing the housing while flexible tubing 22 is joined to the housing by receipt on a section of reduced diameter 18. An interference fit may be relied upon to hold the tubing in place on the section of reduced diameter, although an adhesive may be additionally used.

Figures 2, 2A, 2B, 3, 4:
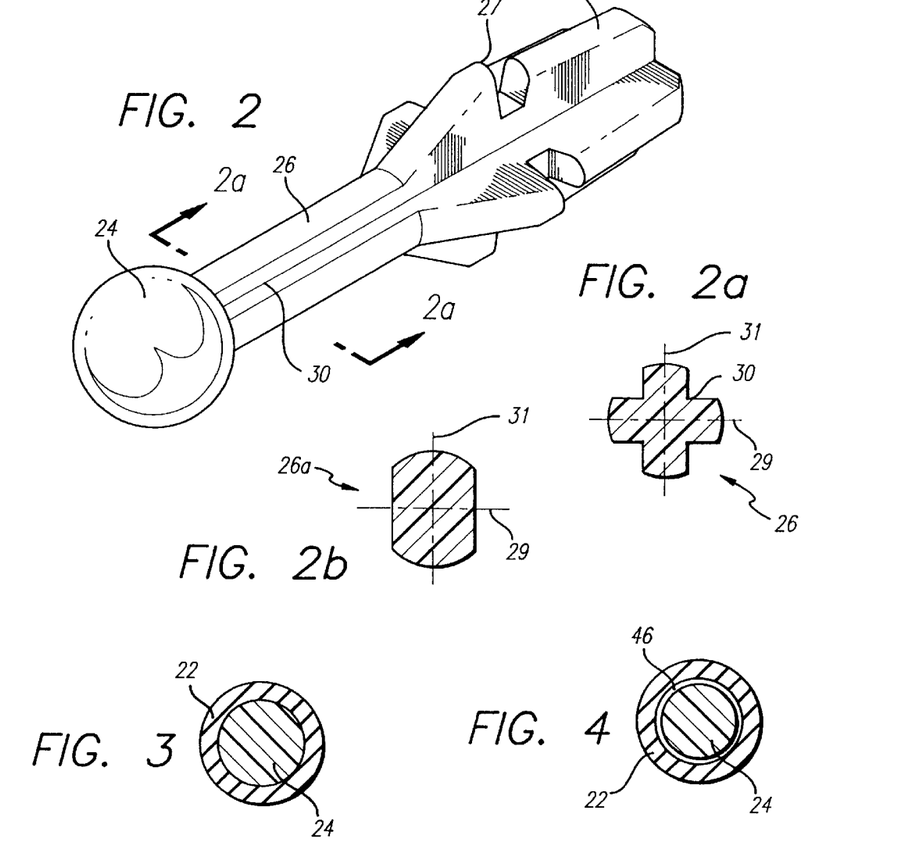
FIG. 2 is a greatly enlarged perspective view of the sealing element including the stem and anchor section.
FIG. 2a is a cross-sectional view taken along line 2a—2a of FIG. 2.
FIG. 2b is a cross-sectional view of an alternative embodiment of the sealing element.
FIG. 3 is a cross-sectional view taken along line 3—3 of FIG. 1 showing the valve in its closed state wherein the tubing sealingly surrounds the sealing element.
FIG. 4 is a cross-sectional view similar to FIG. 3, showing the valve in its open state when internal fluid pressure exceeds the valve's cracking pressure.

A spherical sealing element 24, shown greatly enlarged in FIG. 2, is disposed within the tubing 22 and held in position by a stem 26 that is joined to the housing by an anchor section 28. The diameter of the spherical sealing element is selected to be large enough to engage the inner wall of the tubing by its sealing surface with sufficient force to form a seal as is shown in FIG. 3. Moreover, such diameter is further selected such that a preselected "cracking pressure" exerted by fluid within the tubing is required to sufficiently expand the diameter of tubing to permit the flow of fluid past the sealing surface.

The anchor section is dimensioned to form an interference fit with the housing upon insertion into the bore and may also be held in place by an adhesive. Longitudinal grooves 30 formed on the exterior of the stem and anchor section provide flow paths that set the bore into fluid communication with the tubing lumen. The enlarged portion 27 distal to the anchor section 28 facilitates the assembly of the valve in that it causes the stem to bottom out upon insertion into the bore.

FIG. 2a is a cross-sectional view of one embodiment of the stem 26. In the embodiment shown, the stem is generally non-flexible in that it is formed of a relatively rigid material and has four grooves 30 each of which is equal in size and shape to the others. The orthogonal axes 29 and 31 are preferably equal. Because the stem is relatively rigid, it will not bend significantly when the tubing is pulled laterally in relation to the spherical sealing element during operation of a pump operating on the tubing. This lateral pulling or bending of the tubing will therefore result in a lowered cracking pressure of the valve.

FIG. 2b shows a cross-section of an alternative, more flexible embodiment of the stem 26b. In this case, the stem is formed of a more resilient material. This choice of materials will have the benefit that the stem will tend to bend along an axis 29 so that the stem can follow the longitudinal axis of the tubing as it is bent during installation or mounting of the tubing and valve in a peristaltic pump for operation. As is described below, when mounting the valve in the pump, off-axis force may be encountered that will cause the tubing to bend in relation to the ball. If the stem does not also bend, the cracking pressure will be lowered. If the cracking pressure is lowered enough due to this bending, the valve may open and some fluid from upstream may pass or leak through the valve. This is an undesirable event in the case of certain highly potent drugs. In the embodiment shown in FIG. 2b, a more resilient material is used for the stem and it will tend to bend along axis 29 with the tubing as they are mounted into the pump. Because the stem will bend with the tubing, the cracking pressure will be maintained at its desired level and leakage will not occur.

However, it remains desirable to have a lowered cracking pressure in the orthogonal axis 31 during operation of the valve by a peristaltic mechanism, as will be described below in more detail. To cause the cracking pressure to lower in this axis 31, the stem is formed with a larger amount of material in that axis as shown in FIG. 2b, resulting in increased rigidity in that axis 31. The stem will not bend with the tubing as the tubing is pulled laterally by the peristaltic mechanism during operation and the cracking pressure will therefore be lowered.

Figure 5:
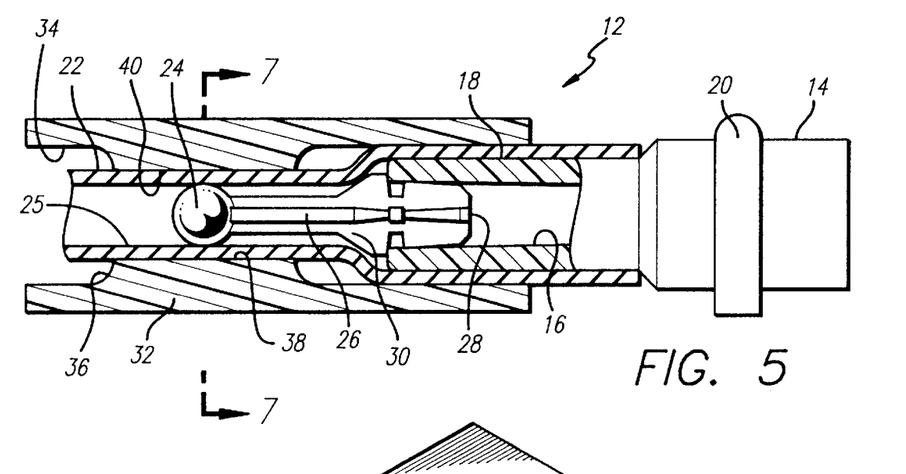
FIG. 5 is a cross-sectional view of the valve with an actuator element in position to open the valve for fluid flow.
Figure 6:
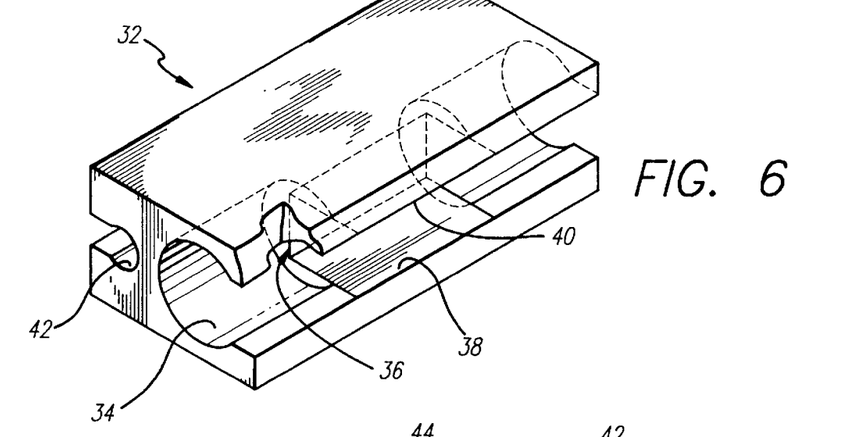
FIG. 6 is an enlarged perspective view of one embodiment of an actuator element for maintaining the valve in its open state.
Figure 7:
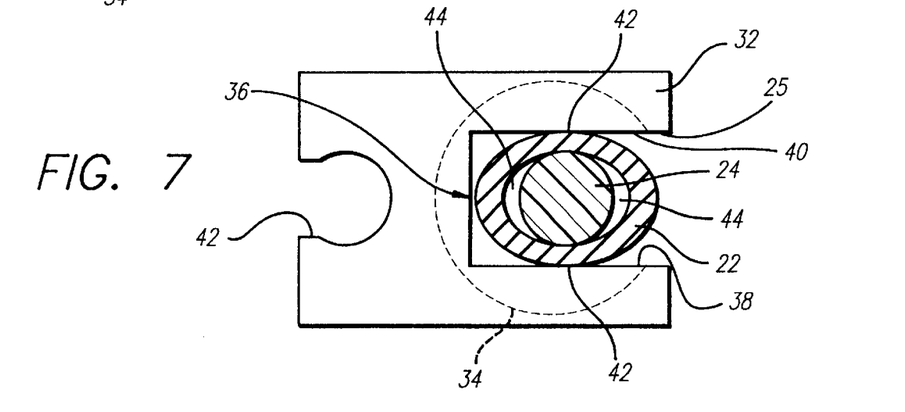
FIG. 7 is a cross-sectional view taken along line 7—7 of FIG. 5, showing the interaction of the actuator element with the tubing to form fluid paths around the sealing element.

FIGS. 5 and 7 illustrate the valve 12 of the present invention with the actuator element 32 in place. The actuator element, shown in perspective in FIG. 6, includes a longitudinal groove 34 of circular cross-section, that generally corresponds in diameter to the diameter of the tubing as received on the section of reduced diameter 18 of the housing 14. Near the center of the actuator element is a section 36 of reduced, cross-section. The center section comprises a generally square groove wherein the gap between opposing surface 38, 40 is less than the outer diameter of the resiliently deformable tubing 22 in its relaxed state, yet greater than the diameter of the sealing surface 24. The opposite side of the actuator element has a second groove 42 formed therein also of circular cross-section that is sized to receive the tubing of the IV set. The actuator element is symmetrical end to end so as to be receivable by the valve element in either orientation.

Various materials may be used in the construction of the valve apparatus 12 of the present invention. In a preferred embodiment, the valve housing 14 comprises molded polyvinyl chloride, the spherical sealing element 24, stem 26, and anchor section 28 comprise a single molding of ABS resin and the actuator element 32 comprises molded CYROLITE G-20. An adequate amount of deformability and resiliency is imparted to the tubing 22 with the use of extruded silicone rubber. For the more flexible embodiment shown in FIG. 2b, the sealing element 24, stem, 26, and anchor section 28 are preferably formed of a highly resilient material, such as a styrene-butadiene copolymer.

As is shown in FIG. 3, the valve is closed when the fluid pressure within the tubing is below the cracking pressure and the actuator element 32 is absent from about the sealing element. The interference fit between the sealing element 24 and the tubing 22 serves to form a seal and maintain such seal when subjected to the maximum head pressure that would be exerted thereon by an administration set, such as a gravity-driven administration set. When the pressure within the tubing upstream of the valve exceeds the cracking pressure, the tube expands to a diameter greater than the sealing element 24 and fluid can flow freely between the sealing element 24 and the inside of the tubing, as shown in FIG. 4.

The valve configuration of the present invention avails two different modes of operation, one manual and one automatic. In the manual mode of operation, the actuator element 32 is slipped onto the tubing 22 such that the section of reduced diameter 36 is positioned about the sealing element 24 as is shown in FIGS. 5 and 7. In FIG. 5, the actuator element 32 has been slid over the tubing 22, sealing member 24, and is partially over the housing. The reduced diameter portion 25 of the actuator element 32 has a length selected so that if the actuator element were slid until contact were made between its reduced diameter portion 25 and the reduced diameter portion 18 of the housing, the reduced diameter portion 25 of the actuator element would be over the sealing element 24 and flow would occur. This makes it much easier to know when the actuator element is in the correct position for causing flow as the operator need only mount it onto the tubing above the housing and slide it towards the housing until it stops.

Figure 9:
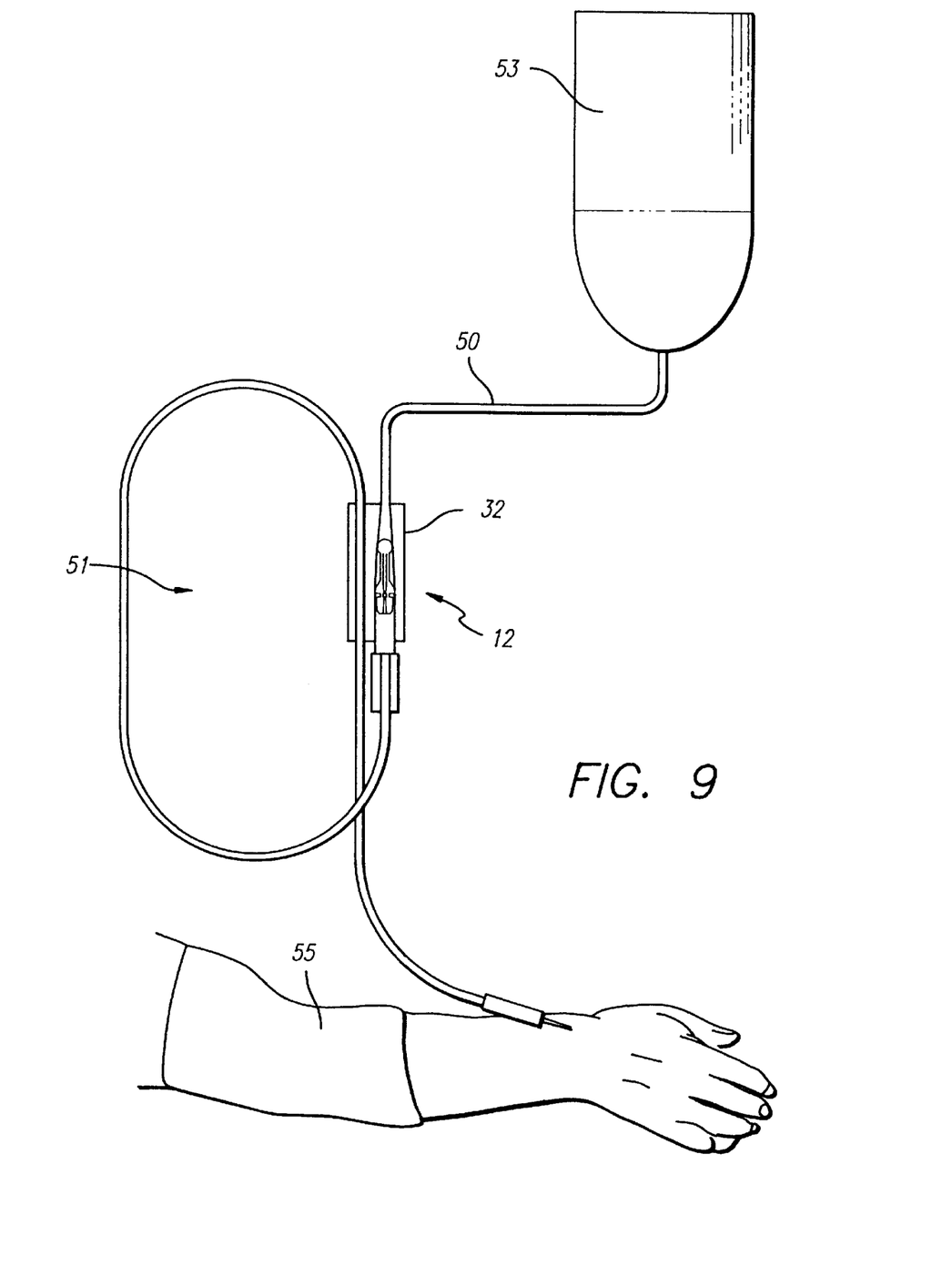
FIG. 9 is a perspective view showing the valve apparatus being used in a gravity feed configuration wherein the valve is actuated to the flow configuration by engagement of the actuator element.

As is visible in FIG. 7, the actuator element causes pressure to be exerted on the tubing at two diametrically opposed points 42 which in turn causes the tubing to deform and create two fluid paths 44 on either side of the sealing element (FIG. 7). The valve is thus in its open state and remains in such state until the actuator element 32 is removed. This mode of operation is used when purging an IV set of air prior to infusion or for administering fluid by gravity feed. As is shown in FIG. 9, the valve may be used to control the flow of fluid through an IV set 50.

In one embodiment, the actuator element 32 is permanently attached to the IV set downstream from the valve by receipt of the IV line in the second groove 42. The groove is small enough to grip the tubing so that the actuator element does not slide down the tubing but adhesive may also be used to hold it in place. The use of adhesive would provide more assurance that the actuator element will not become lost and then unavailable when needed. By forming a loop 51, the groove 34 becomes aligned with the valve 12 to allow the section of reduced diameter to be forced onto the tubing about the valve member 24. This serves to maintain the valve open without further or continued manipulation.

The valve functions in its automatic mode of operation without benefit of any external hardware by virtue of the carefully selected diameter of the sealing surface relative to the inner diameter of the deformable tubing 22 and the resiliency of such tubing. As internal fluid pressure is increased, the diameter of the tubing increases in reaction thereto. When the cracking pressure is achieved, the inner surface of the tubing parts from the sealing surface to form a flow path 46 there about as is shown in FIG. 4. Decrease of the fluid pressure below the cracking pressure allows the tubing to relax and re-establish a seal as per FIG. 3.

Figure 8:
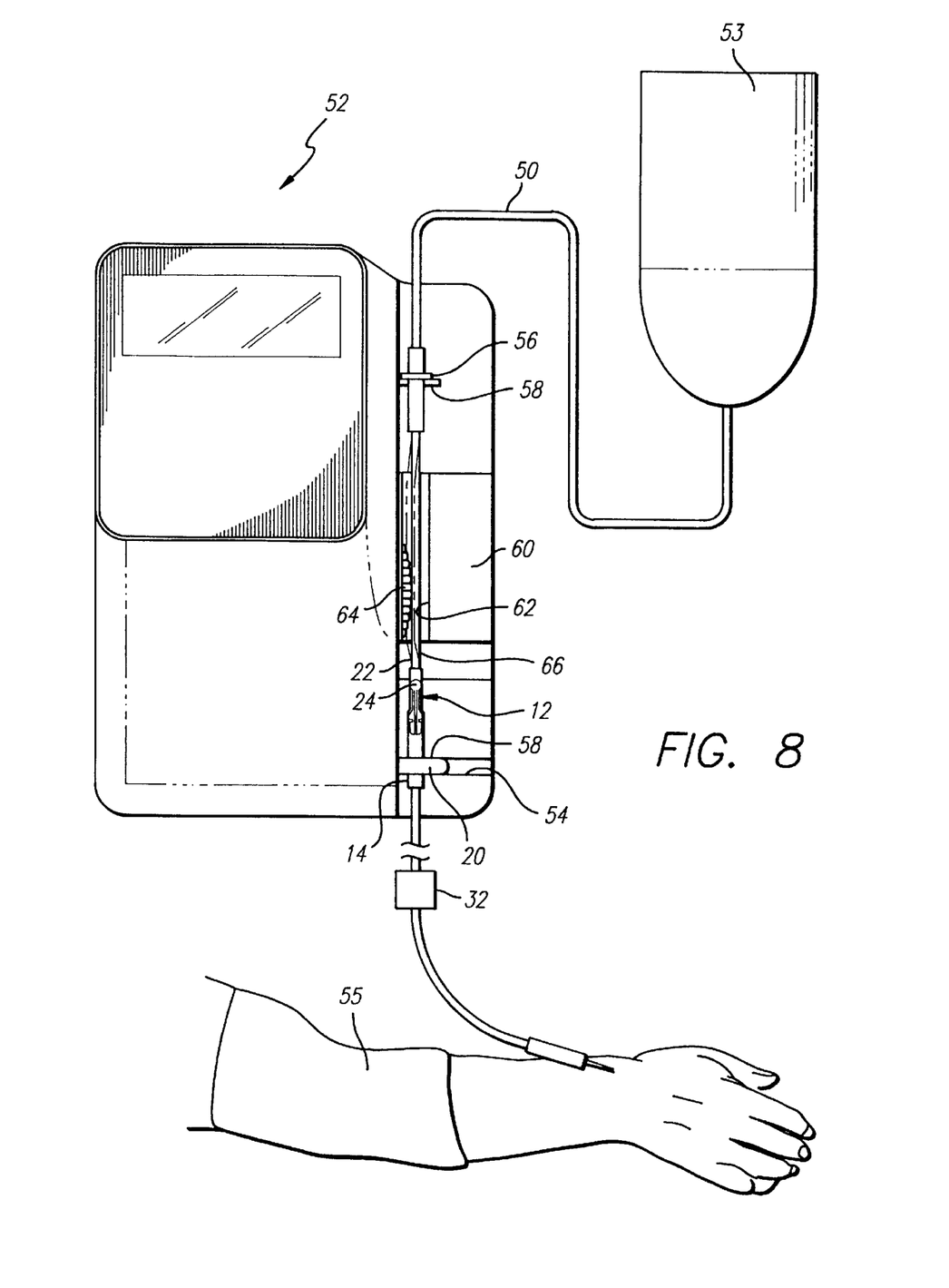
FIG. 8 is a cross-sectional view of the valve apparatus of the present invention in use within a peristaltic pump showing the housing immobilized by a bracket and the tubing displaced laterally in relation to the stem and seal element to engage pumping fingers.

FIG. 8 illustrates a valve 12 in accordance with the present invention installed in line in an IV set 50 and manipulated by a linear peristaltic pump 52. The pump serves to meter the flow of fluid from the elevated reservoir 53 to the patient 55. The mounting bracket 54 formed in the pump housing cooperates with the collar 20 of the valve housing to immobilize the valve housing 14 while a fitting 56 installed upstream in line within the IV set is similarly immobilized by a bracket 58. Such installation subjects the tubing 22 to tension. The tubing is routed through the pumping section 60 and when the pressure pad 62 is moved into position so as to urge the tubing against the pumping fingers 64 of the linear peristaltic mechanism, the tubing is laterally displaced at 66 in relation to the ball 24 (the tubing is pulled to the left in the diagram). The lateral displacement of the tubing in conjunction with the tension the tubing is under and the relative rigidity of the stem cause the tubing to be stretched off axis and serve to reduce the valve's cracking pressure, although cracking pressure is still greater than the head pressure generated by the IV set. Thus, the valve remains closed until sufficient pressure is generated by the pump and immediately re-closes as the pressure drops below the cracking pressure. This serves the function of only providing a flow path when adequate pressure is generated by the pump. Thus, simply being installed in the pump does not serve to open a flow path and as a result, a malfunctioning pump, such as one wherein a peristaltic finger does not completely occlude the pump during its operational cycle, or a misloaded tubing in the pump, would not result in free flow. The patient is thereby protected from over-infusion.

The radial edges of the anchor section are dimensioned to provide an interference fit within the housing. The enlarged portion 27 of the stem is sized to prevent the over-insertion of the stem into the housing 14 upon assembly. The stem 26 is oriented in relation to the housing and the collar 20 so that the forces generated by the lateral displacement of the tubing by the pressure pad 62 are aligned with the less flexible dimension 31 of the stem, in the embodiment of FIG. 2*b*. This allows the cracking pressure to be reduced from about 10 psi to 1½ psi as the tubing is pulled laterally. However, in mounting the valve in a bracket on the peristaltic pump having the configuration shown in FIG. 8, the tubing, sealing element, and stem must be pressed in first at an angle. In the embodiment of FIG. 2*b* where a more resilient plastic material is used for the stem and the stem is oriented so that the narrower axis 29 will experience any bending force associated with the mounting process, the stem will flex along the axis 29 with the tubing during mounting and the seal will be maintained. Flexibility in this direction or axis 29 allows the valve to be more easily installed in the housing as shown in FIG. 8. The deeply grooved surface of the stem and anchor shown in FIG. 2*a* serves to maximize the flow of fluid within the housing.

Thus there has been provided a new and novel valve apparatus. At least three modes of operation are available with this apparatus. In a first mode, manual activation of the valve, such as by pinching the tubing around the ball with one's finger and thumb, will result in gravity flow. In a second mode, the valve may be activated by the actuator element shown in FIG. 6 for gravity flow. In a third mode, the valve is activated by pump-powered flow providing pressure at or above the cracking pressure.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A valve for use with an IV set subject to a head pressure and a pumping pressure, wherein said pumping pressure is higher than said head pressure, comprising:

a housing having formed therein a bore for conducting fluid therethrough;

resiliently deformable tubing attached to said housing so as to be in fluid communication with said bore, said tubing having an inner and an outer diameter; and     a sealing element comprising a spherical sealing surface, said sealing element being affixed to said housing by a stem that is fixedly received within said bore such that said sealing surface is positioned within said tubing and wherein said sealing surface is dimensioned to engage said tubing and maintain a seal when said tubing is subjected to an internal pressure below a cracking pressure wherein said cracking pressure is greater than said head pressure and less than said pumping pressure;

wherein said stem has an outer surface containing a longitudinal groove having a depth such that fluid may flow around the stem.

2. The valve of claim 1 wherein said sealing element is positioned upstream of said housing.

3. The valve of claim 1 wherein said housing has an exterior shaped so as to be immobilized upon receipt in a bracket disposed in a peristaltic pump.

4. The valve of claim 1 further comprising an actuator element having two opposed parallel surfaces spaced apart by a distance less than the outer diameter of said tubing and greater than the diameter of said sealing surface wherein said actuator element is configured to be removably attachable to said tubing such that said opposed surfaces cause said tubing to be compressed against said sealing surface.

5. The valve of claim 4 wherein said actuator element is configured to engage said housing while attached to said tubing.

6. The valve of claim 4 wherein said actuator element is symmetrical so as to be attachable to said tubing in two different orientations.

7. The valve of claim 4 wherein said actuator element is permanently attached to said IV set.

8. The valve of claim 7 wherein said actuator element is attached to said IV set downstream from said housing.

9. The valve of claim 7 wherein said actuator element has a groove formed therein dimensioned to receive a conduit forming part of said IV set.

10. The valve of claim 1 wherein the stem comprises two orthogonal axes with a first axis being formed such that it provides less flexibility to the stem than the orthogonal axis has, when subjected to force along said first axis.

11. The valve of claim 10 wherein the stem comprises a larger cross-section in the first axis thereby allowing less flexibility than in the orthogonal axis.

12. A valve for use with an IV set subject to a head pressure and a pumping pressure, wherein said pumping pressure is higher than said head pressure, comprising:
  a housing having formed therein a bore for conducting fluid therethrough;
  resiliently deformable tubing attached to said housing so as to be in fluid communication with said bore, said tubing having an inner and an outer diameter; and
  a sealing element having a sealing surface, said sealing element being affixed to said housing by a stem that is fixedly received within said bore such that said sealing surface is positioned within said tubing and wherein said sealing surface is dimensioned to engage said tubing and maintain a seal when said tubing is subjected to an internal pressure below a cracking pressure wherein said cracking pressure is greater than said head pressure and less than said pumping pressure;
  wherein the stem comprises two orthogonal axes with a first axis being formed such that it provides less flexibility to the stem than the orthogonal axis has, when subjected to force along said first axis.

13. The valve of claim 12 wherein the stem comprises a larger cross-section in the first axis thereby allowing less flexibility than in the orthogonal axis.

14. A valve for use with an IV set subject to a head pressure and a pumping pressure, wherein said pumping pressure is higher than said head pressure comprising:
  a housing having formed therein a bore for conducting fluid therethrough;
  resiliently deformable tubing attached to said housing so as to be in fluid communication with said bore, said tubing having an inner and an outer diameter;
  a sealing element having a sealing surface, said sealing element being affixed to said housing such that said sealing surface is positioned within said tubing and wherein said sealing surface is dimensioned to engage said tubing and maintain a seal when said tubing is subjected to an internal pressure below a cracking pressure wherein said cracking pressure is greater than said head pressure and less than said pumping pressure; and
  an actuator element having two opposed parallel surfaces spaced apart by a distance less than the outer diameter of said tubing and greater than the diameter of said sealing surface wherein said actuator element is configured to be removably attached to said tubing such that said opposed surfaces cause said tubing to be compressed against said sealing surface, and wherein said actuator element is permanently attached to said IV set and wherein said actuator element has a groove formed therein dimensioned to receive a conduit forming part of said IV set.

15. A valve, comprising:
  a housing having formed therein a bore for conducting fluid therethrough;
  resiliently deformable tubing attached to said housing so as to be in fluid communication with said bore, said tubing having an inner and an outer diameter;
  a sealing element comprising a spherical sealing surface, said sealing element being rigidly affixed to said housing by a stem that is fixedly received within said bore such that said sealing surface is positioned within said tubing and wherein said spherical surface is dimensioned to engage said tubing and form a seal;
  wherein said stem has an outer surface containing a longitudinal groove having a depth such that fluid may flow around the stem; and
  an actuator element removably fitable to said tubing about said sealing element, wherein said actuator element has two opposed parallel surfaces spaced so as to compress said tubing against opposite sides when fitted to said tubes of said sealing surface, to form fluid paths past said sealing surface.

16. The valve of claim 1 wherein said sealing element is positioned upstream of said housing.

17. The valve of claim 15 wherein said actuator element is configured to also engage said housing while attached to said tubing about said sealing element.

18. The valve of claim 15 wherein said actuator element is symmetrical so as to be attachable to said tubing in two different orientations.

19. The valve of claim 15 wherein said actuator element is attached to said IV set.

20. The valve of claim 19 wherein said actuator element is attached to said IV set downstream from said housing.

21. The valve of claim 19 wherein said actuator element has a groove formed therein dimensioned to receive a conduit forming part of said IV set.

22. The valve of claim 15 wherein the stem comprises two orthogonal axes with a first axis being formed such that it provides less flexibility to the stem than the orthogonal axis has, when subjected to force along said first axis.

23. The valve of claim 22 wherein the stem comprises a larger cross-section in the first axis thereby allowing less flexibility than in the orthogonal axis.

24. A valve, comprising:
  a housing having formed therein a bore for conducting fluid therethrough;
  resiliently deformable tubing attached to said housing so as to be in fluid communication with said bore, said tubing having an inner and an outer diameter;
  a sealing element having a sealing surface, said sealing element being rigidly affixed to said housing by a stem that is fixedly received within said bore such that said sealing surface is positioned within said tubing and wherein said spherical surface is dimensioned to engage said tubing and form a seal; and
  an actuator element removably fitable to said tubing about said sealing element, wherein said actuator element has two opposed parallel surfaces spaced so as to compress said tubing against opposite sides when fitted to said tubes of said sealing surface, to form fluid paths past said sealing surface;
  wherein the stem comprises two orthogonal axes with a first axis being formed such that it provides less flexibility to the stem than the orthogonal axis has, when subjected to force along said first axis.

25. The valve of claim 24 wherein the stem comprises a larger cross-section in the first axis thereby allowing less flexibility than in the orthogonal axis.

26. A valve, comprising:
a housing having formed therein a bore for conducting fluid therethrough;
resiliently deformable tubing attached to said housing so as to be in fluid communication with said bore, said tubing having an inner and an outer diameter;
a sealing element having a sealing surface, said sealing element being rigidly affixed to said housing such that said sealing surface is positioned within said tubing and wherein said spherical surface is dimensioned to engage said tubing and form a seal; and
an actuator element attached to said IV set and removably fitable to said tubing about said sealing element, wherein said actuator element has two opposed parallel surfaces spaced so as to compress said tubing against opposite sides when fitted to said tubes of said sealing surface, to form fluid paths past said sealing surface;
wherein said actuator element has a groove formed therein dimensioned to receive a conduit forming part of said IV set.

27. A fluid administration set for conducting fluids to a patient, the set comprising:
a first tubing; and
a valve for use with an IV set subject to a head pressure and a pumping pressure, wherein said pumping pressure is higher than said head pressure, comprising:
a housing having formed therein a bore for conducting fluid therethrough;
resiliently deformable second tubing attached to said housing so as to be in fluid communication with said bore, said second tubing having an inner and an outer diameter and being coupled to the first tubing for conducting fluid from the first tubing to the bore; and
a sealing element comprising a spherical sealing surface, said sealing element being rigidly affixed to said housing by a stem that is fixedly received within said bore such that said sealing surface is positioned within said second tubing and wherein said sealing surface is dimensioned to engage said second tubing and maintain a seal when said second tubing is subjected to an internal pressure below a cracking pressure wherein said cracking pressure is greater than said head pressure and less than said pumping pressure;
wherein said stem has an outer surface containing a longitudinal groove having a depth such that fluid may flow around the stem.

28. The administration set of claim 1 wherein said sealing element is positioned upstream of said housing.

29. The administration set of claim 27 wherein said housing has an exterior shaped so as to be immobilized upon receipt in bracket disposed in a peristaltic pump.

30. The administration set of claim 27 further comprising an actuator element having two opposed parallel surfaces spaced apart by a distance less than the outer diameter of said second tubing and greater than the diameter of said sealing surface wherein said actuator element is configured to be removably attachable to said second tubing such that said opposed surfaces cause said second tubing to be compressed against said sealing surface.

31. The administration set of claim 30 wherein said actuator element is configured to engage said housing while attached to said second tubing.

32. The administration set of claim 30 wherein said actuator element is symmetrical so as to be attachable to said second tubing in two different orientations.

33. The administration set of claim 30 wherein said actuator element is permanently attached to said first tubing.

34. The administration set of claim 33 wherein said actuator element is attached to said first tubing downstream from said housing.

35. The administration set of claim 33 wherein said actuator element has a groove formed therein dimensioned to receive the first tubing.

36. The valve of claim 27 wherein the stem comprises two orthogonal axes with a first axis being formed such that it provides less flexibility to the stem than the orthogonal axis has, when subjected to force along said first axis.

37. The valve of claim 36 wherein the stem comprises a larger cross-section in the first axis thereby allowing less flexibility than in the orthogonal axis.

38. A fluid administration set for conducting fluids to a patient, the set comprising:
a first tubing; and
a valve for use with an IV set subject to a head pressure and a pumping pressure, wherein said pumping pressure is higher than said head pressure, comprising:
a housing, having formed therein a bore for conducting fluid therethrough;
resiliently deformable second tubing attached to said housing so as to be in fluid communication with said bore, said second tubing having an inner and an outer diameter and being coupled to the first tubing for conducting fluid from the first tubing to the bore; and
a sealing element having a sealing surface, said sealing element being rigidly affixed to said housing by a stem that is fixedly received within said bore such that said sealing surface is positioned within said second tubing and wherein said sealing surface is dimensioned to engage said second tubing and maintain a seal when said second tubing is subjected to an internal pressure below a cracking pressure wherein said cracking pressure is greater than said head pressure and less than said pumping pressure;
wherein the stem comprises two orthogonal axes with a first axis being formed such that it provides less flexibility to the stem than the orthogonal axis has, when subjected to force along said first axis.

39. The administration set of claim 38 wherein the stem comprises a larger cross-section in the first axis thereby allowing less flexibility than in the orthogonal axis.

40. A fluid administration set for conducting fluids to a patient, the set comprising:
a first tubing;
a valve for use with an IV set subject to a head pressure and a pumping pressure, wherein said pumping pressure is higher than said head pressure, comprising:
a housing having formed therein a bore for conducting fluid therethrough;
resiliently deformable second tubing attached to said housing so as to be in fluid communication with said bore, said second tubing having an inner and an outer diameter and being coupled to the first tubing for conducting fluid from the first tubing to the bore; and
a sealing element having a sealing surface, said sealing element being rigidly affixed to said housing such that said sealing surface is positioned within said second tubing and wherein said sealing surface is dimensioned to engage said second tubing and maintain a seal when said second tubing is subjected to an internal pressure below a cracking pressure wherein said cracking pressure is greater than said head pressure and less than said pumping pressure; and an actuator element permanently attached to said first tubing and having two opposed parallel surfaces spaced apart by a distance less than the outer diameter of said second tubing and greater than the diameter of said sealing surface wherein said actuator element is configured to be removably attachable to said second tubing such that said opposed surfaces cause said second tubing to be compressed against said sealing surface;

wherein said actuator element has a groove formed therein dimensioned to receive the first tubing.

* * * * *